(12) United States Patent
Albritton, IV

(10) Patent No.: US 9,533,021 B2
(45) Date of Patent: Jan. 3, 2017

(54) NUTRITIONAL SUPPLEMENT

(71) Applicant: Ford D. Albritton, IV, Dallas, TX (US)

(72) Inventor: Ford D. Albritton, IV, Dallas, TX (US)

(73) Assignee: Sustain Biologics, LLC, Dallas, TX (US)

( * ) Notice: Subject to any disclaimer, the term of this patent is extended or adjusted under 35 U.S.C. 154(b) by 0 days.

(21) Appl. No.: 14/030,753

(22) Filed: Sep. 18, 2013

(65) Prior Publication Data

US 2015/0079060 A1 Mar. 19, 2015

Related U.S. Application Data

(63) Continuation of application No. 13/245,616, filed on Sep. 26, 2011, now abandoned, which is a continuation of application No. 11/897,985, filed on Aug. 31, 2007, now abandoned.

(51) Int. Cl.

| | | |
|---|---|---|
| *A23L 1/30* | (2006.01) | |
| *A23L 1/302* | (2006.01) | |
| *A61K 31/05* | (2006.01) | |
| *A61K 31/122* | (2006.01) | |
| *A61K 31/198* | (2006.01) | |
| *A61K 31/353* | (2006.01) | |
| *A61K 31/385* | (2006.01) | |
| *A61K 31/51* | (2006.01) | |
| *A61K 31/519* | (2006.01) | |
| *A61K 31/675* | (2006.01) | |
| *A61K 31/7048* | (2006.01) | |
| *A61K 33/00* | (2006.01) | |
| *A61K 36/9068* | (2006.01) | |
| *A61K 31/225* | (2006.01) | |
| *A61K 31/714* | (2006.01) | |
| *A61K 33/08* | (2006.01) | |
| *A61K 36/82* | (2006.01) | |

(52) U.S. Cl.
CPC ............ *A61K 36/9068* (2013.01); *A23L 33/10* (2016.08); *A23L 33/105* (2016.08); *A23L 33/12* (2016.08); *A23L 33/15* (2016.08); *A23L 33/175* (2016.08); *A61K 31/05* (2013.01); *A61K 31/122* (2013.01); *A61K 31/198* (2013.01); *A61K 31/225* (2013.01); *A61K 31/353* (2013.01); *A61K 31/385* (2013.01); *A61K 31/51* (2013.01); *A61K 31/519* (2013.01); *A61K 31/675* (2013.01); *A61K 31/7048* (2013.01); *A61K 31/714* (2013.01); *A61K 33/00* (2013.01); *A61K 33/08* (2013.01); *A61K 36/82* (2013.01)

(58) Field of Classification Search
CPC ........ A23L 1/30; A23L 1/3002; A23L 1/3008; A23L 1/302; A23L 1/3051; A61K 31/05; A61K 31/122; A61K 31/198; A61K 31/225; A61K 31/353; A61K 31/385; A61K 31/51; A61K 31/519; A61K 31/675; A61K 31/7048; A61K 31/714; A61K 33/00; A61K 33/08; A61K 36/82

See application file for complete search history.

(56) References Cited

U.S. PATENT DOCUMENTS

| | | |
|---|---|---|
| 3,422,186 A | 1/1969 | Sasmor |
| 4,740,373 A | 4/1988 | Kesselman et al. |
| 5,977,162 A | 11/1999 | Seidman |
| 6,066,652 A | 5/2000 | Zenner et al. |
| 6,093,417 A | 7/2000 | Petrus |
| 6,177,434 B1 | 1/2001 | Kopke et al. |
| 6,733,797 B1 | 5/2004 | Summers |
| 6,815,434 B2 | 11/2004 | Kil et al. |
| 2004/0047896 A1 | 3/2004 | Malnoe et al. |
| 2004/0131656 A1 | 7/2004 | Roufs et al. |
| 2005/0107338 A1 | 5/2005 | Seidman |
| 2006/0040000 A1 | 2/2006 | Gokaraju et al. |
| 2006/0257502 A1 | 11/2006 | Liu |
| 2007/0116839 A1 | 5/2007 | Prakash et al. |

FOREIGN PATENT DOCUMENTS

WO WO 2006/121985 11/2006

OTHER PUBLICATIONS

Raponi et al. (Abstract of: Int Tinnitus J. 2003;9(2):104-8).*
Takumida et al. (Abstract of: Acta Otolaryngol 2003;123(6):697-703).*
Diao et al. (Abstract of: Sheng Li Xue Bao 2003;55(6):672-6).*
Kopke et al. (Abstract of: Acta Otolaryngol 2005;125(3):235-43).*
Sato (Abstract of: Acta Otolaryngol Suppl. 1988;458:95-102).*
Henderson et al. (Annals of the NYAS. 2006;884(1):368-379).*
Sensorineural hearing loss [online] retrieved on Jan. 20, 2016 from: http://www.asha.org/public/hearing/Sensorineural-Hearing-Loss/; 1 page.*
International Search Report dated Dec. 16, 2008 in connection with PCT Application No. PCT/US08/74913.
Written Opinion of the International Searching Authority dated Dec. 16, 2008 in connection with PCT Application No. PCT/US08/74913.

(Continued)

*Primary Examiner* — Ernst V Arnold
(74) *Attorney, Agent, or Firm* — Winstead PC

(57) ABSTRACT

A nutritional supplement for inhibiting sensorineural hearing loss includes from about 0.25 to about 6.0 wt. % thiamin, from about 0.1 to about 10 wt. % pyridoxiyl-5-phosphate, from about 0.01 to about 10 wt. % folic acid, from about 0.025 to about 4.0 wt. % hydroxycobalamin, from about 1 to about 7 wt. % magnesium, from about 0.25 to about 6.0 wt. % zinc, from about 0.001 to about 0.02 wt. % selenium, from about 0.1 to about 10 wt. % manganese, from about 5 to about 50 wt. % ginger root P.E. 4:1, from about 5 to about 40 wt. % citrus bioflavonoids, from about 2.5 to about 40 wt. % l-cystine, from about 5 to about 40 wt. % n-acetyl-l-carnitine, from about 1 to about 40 wt. % alpha lipoic acid, from about 1 to about 40 wt. % coenzyme Q10, from about 1 to about 40 wt. % green tea extract, and from about 1 to about 60 wt. % resveratrol.

6 Claims, No Drawings

(56) References Cited

OTHER PUBLICATIONS

MedlinePlus Trecher-Collin syndrome, retrieved from http://www.nlm.nih.gov/medlineplus/ency/article/001659.htm on Feb. 28, 2010, 2 pages.

MedlinePlus tinnitus, retrieved from http?///www.nlm.nih.gov/medlineplus/ency/article/003043.htm on Feb. 25, 2010, 3 pages.

Antonio, et al., Inner Ear, Genetic Sensorineural Hearling Loss, retrieved from http://emedicine.medscape.com/article/855875-print on Feb. 25, 2010, 14 pages.

Dictionary MSN Encarta, Inhibit, retrieved from http://encarta.msn.com/encnet/features/dictionary/DictionaryResults.aspx?refid=1861621305 on Mar. 1, 2010, 3 page.

Supplement Search Report dated Oct. 25, 2005 in connection with European Application No. 08828520.

* cited by examiner

NUTRITIONAL SUPPLEMENT

CROSS REFERENCE TO RELATED APPLICATIONS

This application is a continuation of U.S. patent application Ser. No. 13/245,616 filed on Sep. 26, 2011 which is a continuation of U.S. patent application Ser. No. 11/897,985 filed on Aug. 31, 2007 (abandoned), and which are incorporated herein by reference.

TECHNICAL FIELD

The disclosure relates to nutritional supplements and, in particular, to nutritional supplements that protect the inner ear and inhibit or alleviate sensorineural hearing loss.

BACKGROUND

Sensorineural hearing loss results from damage to or deterioration of the inner ear (sensory loss) and/or damage to the auditory nerve (neural loss) which conducts the signals to the brain. Sensorineural hearing loss can be caused by diseases, birth injury, drugs that are toxic to the auditory system, and genetic syndromes. Sensorineural hearing loss may also occur as a result of noise exposure, viruses, head trauma, aging, and tumors. Except in the case of a sudden onset of hearing loss due to certain injuries, sensorineural hearing loss is generally not reversible.

It has been estimated that 80% of all cases of hearing loss are sensorineural. In the United States alone, it is believed that more than twenty two million people have enough sensorineural hearing loss to affect their ability to communicate. This form of hearing loss is particularly devastating because it affects the ability to discriminate between sounds and understand complex combinations of sounds, including speech.

Generally, sensorineural hearing loss is a cumulative disease caused by a wide range of genetic and environmental factors. The effects of these factors include degradation of the myelin sheaths enclosing auditory nerves, neurological plaque formation causing cell/neuron death/dysfunction, and cochlear receptor cell death. An individual's genetics determine the threshold resistance of the cochlear system and associated neurons to cumulative damage before the effect of environmental and external factors. Predisposition to sensorineural hearing loss may be evidenced by ear-specific genetic variations that may be inherited variations, whether dominant, recessive and/or sex-linked. Some individuals may have a genetic predisposition to spontaneous mutation.

Known genetic variations may have a number of effects contributing to sensorineural hearing loss. These variations may result in improper enzyme or cell physiology including deficient enzyme function in neural myelination, ineffective or malformed membrane transporters for intracellular nutrients such as thiamine, poor native production of native anti-oxidants such as dismutases and synthases. Other effects may include increased production of super-oxides, hydroxyls, and other damaging molecules and radicals, decreased mitochondrial health secondary to genetic coded enzyme misconformation and ineffective metabolic degradation of toxins, evidenced in certain individuals that have a greater sensitivity to a type of antibiotics called aminoglycosides.

Genetic variation may result in poor cell membrane stability, impaired cellular microstructure with poor microcirculation exacerbating all of these effects. Systemic genetic diseases such as diabetes may result in the formation of glycation products leading to respiratory burst enzymes e.g., superoxide anions. Similarly, hypertension may result in upregulation of NAD(P)H oxidase, a source of superoxide anions. Superoxides and similar reactive oxygen species can cause oxidative damage to cell structures. Hydroxyl radicals can damage cell membranes and lipoproteins by lipid peroxidation. Radical oxygen species can damage proteins, leading to structural changes and loss of enzyme activity.

Environmental and other external factors may contribute to cumulative damage to inner and outer hair cells, cochlear mitochondria, membrane stability and the vascular supply to cochlea and nerves. Continuous exposure to noise levels above 85 dB will cause gradual hearing loss in some individuals. Even a single exposure to higher noise levels may cause damage. Certain medications such as aminoglycosides, vancomycin, furosamide, and chemotherapeutic agents can damage the cochlea system. Infections such as meningitis, mumps, measles, other viral and bacterial infections, allergic reactions, exposure to ionizing radiation and autoimmune deficiencies can all contribute to sensorineural hearing loss.

The concept that sensorineural hearing loss may result from the cumulative affect of multiple insults prior to manifesting irreversible damage is well recognized and described. These multiple insults gradually wear down the buffer zone between normal auditory function and the onset of hearing loss. Age is associated with hearing loss because longer life translates into more cumulative exposures to causes of the loss. If there is a family history of hearing loss, e.g. a genetic predisposition to any of the many factors that can result in sensorineural hearing loss, the buffer between normal function and deterioration is smaller than in non-genetic cases.

SUMMARY

In one aspect thereof, a nutritional supplement for inhibiting sensorineural hearing loss includes a combination of resveratrol, EGCG, acetyl-1-carnitine, alpha lipoic acid coenzyme Q10, hesperidin in the form of citrus bioflavonoids, and pyridoxiyl-5-phosphate in nutritionally effective amounts. In one embodiment, the supplement includes from about 1-60 wt. % resveratrol, 1-40 wt. % green tea extract, from about 5-40 wt. % acetyl-1-carnitine, from about 1%-40 wt. % alpha lipoic acid, from about 1-40 wt. % coenzyme Q10, from about 5-40 wt. % citrus bioflavonoids and from about 0.1-10 wt. % pyridoxiyl-5-phosphate. This combination of ingredients mitigates or alleviates the effect of trauma, disease, genetic factors and other insults that wear down the buffer zone between normal auditory function and the onset of hearing loss.

In one variation, hesperidin is provided in the form of citrus bioflavonoids comprising about 20 wt. % hesperidin. The green tea extract provides EGCG. In one embodiment, the green tea extract includes 90 wt. % catechins including about 50 wt. % EGCG. The supplement may also include other supportive and synergistically effective ingredients such as ginger root P.E 4:1, folic acid, 1-cysteine, magnesium oxide, zinc, selenium amino acid chelate, and manganese amino acid chelate.

In another variation, the supplement includes a combination of thiamin, pyridoxiyl-5-phosphate, folic acid, hydroxycobalamin, ginger root P.E 4:1, hesperidin, 1-cysteine, n-acetlyl-1-carnitine, alpha lipoic acid, coenzyme Q10, EGCG, and resveratrol in nutritionally effective amounts and wherein the supplement inhibits sensorineural hearing loss. The hesperidin may be citrus bioflavonoids including about 20 wt. % hesperidin and the EGCG is provided in the form of green tea extract. In one variation, the supplement includes: from about 0.25 to about 6.0 wt. % thiamin, from about 0.1 to about 10 wt. % pyridoxiyl-5-phosphate, from about 0.01 to about 10 wt. % folic acid, from about 0.025 to about 4.0 wt. % hydroxycobalamin, from about 5 to about 40 wt. % citrus bioflavonoids, from about 2.5 to about 40 wt. % 1-cystine, from about 5 to about 40 wt. % n-acetlyl-1-carnitine, from about 1 to about 40 wt. % alpha lipoic acid, from about 1 to about 40 wt. % coenzyme Q10, from about 1 to about 40 wt. % green tea extract, and from about 1 to about 60 wt. % resveratrol. The term "about" as used herein encompasses minor variations from the stated percentages due to manufacturing variances, measurement limitations and other factors that may cause minor variances from nominal stated values.

In one variation, the supplement may include from about 1 to about 7 wt. % magnesium, from about 0.25 to about 6.0 wt. % zinc, from about 0.001 to about 0.02 wt. % selenium and from about 0.1 to about 10 wt. % manganese. In another, the supplement may include from about 5 to about 50 wt. % ginger root P.E. 4:1.

In yet another variation including supportive and synergistic ingredients, the supplement includes from about 0.25 to about 6.0 wt. % thiamin, from about 0.1 to about 10 wt. % pyridoxiyl-5-phosphate, from about 0.01 to about 10 wt. % folic acid, from about 0.025 to about 4.0 wt. % hydroxycobalamin, from about 1 to about 7 wt. % magnesium, from about 0.25 to about 6.0 wt. % zinc, from about 0.001 to about 0.02 wt. % selenium, from about 0.1 to about 10 wt. % manganese, from about 5 to about 50 wt. % ginger root P.E. 4:1, from about 5 to about 40 wt. % citrus bioflavonoids, from about 2.5 to about 40 wt. % 1-cystine, from about 5 to about 40 wt. % n-acetlyl-1-carnitine, from about 1 to about 40 wt. % alpha lipoic acid, from about 1 to about 40 wt. % coenzyme Q10, from about 1 to about 40 wt. % green tea extract and from about 1 to about 60 wt. % resveratrol.

DETAILED DESCRIPTION

The dietary supplements disclosed herein represent a multi-faceted approach to protect cochlear and labyrinthine cellular integrity and prevent or slow the onset of sensorineural hearing loss. The supplements include ingredients to protect cochlear and labyrinthine cellular integrity and physiologic function through a wide variety of mechanisms that function on a tissue, cellular, and sub cellular level. The ingredients promote cell membrane stability, cytoprotection from hazardous metabolites including but not restricted to oxygen free radicals, immunologic modification to prevent immune mediated damage to inner ear cells and efficient and appropriate cell messenger system operation. The supplements disclosed herein also aid in regulating apoptosis (planned cell death at senescence) and in protecting and facilitating mitochondrial function, health, and stability. The supplements aid in modulation of platelet function which may include (but not restricted to) reduction of thrombosis of macro and microcirculation.

The supplements disclosed herein also promote improved blood flow via improved vascular smooth muscle function and provide protection from cellular ischemia by promoting production of protective molecules such as adenosine from cells. Additional beneficial effects include promoting proper function of the supporting cells of the inner ears, promoting proper function of cell membrane pumps and other elements maintaining biologic electro-potential of cell fluid spaces, decreasing proinflammatory leukotrienes and prostaglandins and decreasing matrix metalloproteinase 9 (MMP-9), a actor in neuron injury and death and microvascular injury as well as decreasing other harmful proteases.

Other beneficial effects include reducing neural plaque and amyloid formation by reducing or inhibiting plaque production and promoting existing plaque regression. The supplements promote upregulating transcription and production of phase II proteins which are critical in native cellular defense mechanisms (e.g., anti cancer and antioxidant functions) and preventing injury secondary to ischemia through metabolism regulation, decreased tissue activity, and protection during reperfusion.

The supplements disclosed herein use effective amounts of biologically active agents to provide a combination of different effects to promote the longevity and health of the cochlear system. These effects include stimulating circulation and promoting the quantity of microcirculation, e.g., the flow of blood through the smallest vessels of the body. The supplement is formulated to neutralize toxins prior to entering the cochlea and brain and to prevent cochlear ischemia. The supplement includes agents to prevent reperfusion injury and the formation of free radicals in the event of ischemia. Other effects of the supplement include reduction of cell function during periods of stress for preservation. Use of the supplement tends to reduce or reverse inflammation by decreasing immune moderators and decreasing the intensity of immune response to prevent over-response. Other desirable effects include decreasing chronic viral stimulation of the immune system, decreasing the damaging effects of cytotoxic factors and preventing cell death via apoptosis modulation. The supplement further includes biologically active agents to prevent neural plaque and neurotoxic metabolite formation and encourage its breakdown.

In one variation, the supplements may include the following ingredients: thiamin (as thiamin hydrochloride), vitamin B6 (as pyridoxiyl 5 phosphate), folic acid, vitamin B12 (as hydroxycobalamin), magnesium (as magnesium oxide), zinc (as zinc citrate), selenium (as selenium amino acid chelate), manganese (as manganese amino acid chelate), ginger root P.E 4:1, citrus bioflavonoid (40% flavonoids, 20% hesperidin), 1-cysteine, n-acetlyl-1-carnitine, alpha lipoic acid, coenzyme Q10, green tea extract (90% catechins, 50% EGCG) and resveratrol.

In one embodiment, supplements disclosed herein may include from about 0.25 to about 6.0 wt. % Thiamin. Thiamin, also known as vitamin B1, is a water-soluble, crystalline compound of the B complex vitamin group. Thiamin has a well known role in the adenosine triphosphate, or ATP, the body's primary energy-carrying molecule. Thiamin is also essential for the normal functioning of the nervous system due to its role in the synthesis of acetylcholine, a neurotransmitter which can affect many functions including mood and memory.

Supplements disclosed herein may include from about 0.1 to about 10.0 wt. % vitamin B6 as pyridoxiyl-5-phosphate. Vitamin B6 is a water-soluble vitamin that exists in three major chemical forms: pyridoxine, pyridoxal, and pyridoxamine. Vitamin B6 has a well known role in protein synthesis and is required for more over one hundred enzymatic reactions involved in protein metabolism. Adequate levels vitamin B6 are necessary for proper coenzyme Q10 synthesis and function in the body. Vitamin B6 is also needed for the conversion of tryptophan (an amino acid) to niacin (a vitamin) and is essential for red blood cell metabolism.

Vitamin B6 plays a wide variety of roles in supporting the integrity of the nervous system and neurological activity. Vitamin B6 is further required for the synthesis of amine derived neurotransmitters such as serotonin, melatonin, epinephrine and norepinephrine.

Supplements as disclosed herein also may include from about 0.1 to about 10 wt. % folic acid. Folic acid and folate (the anion form) are forms of the water-soluble vitamin B9. The biologically active form of folic acid is tetrahydrofolic acid (THFA), which is derived by a two step reduction of folate involving dihydrofolate reductase. THFA plays a key role in the transfer of 1-carbon units (such as methyl, methylene, and formyl groups) to the essential substrates involved in the synthesis of DNA, RNA, and proteins. Specifically, THFA is involved with the enzymatic reactions necessary to synthesis of purine, thymidine, and amino acids.

Vitamin B12 (methylcobalaamin) is required for the function of the folate-dependent enzyme, methionine synthase. This enzyme is required for the synthesis of the amino acid, methionine, from homocysteine. Methionine in turn is required for the synthesis of S-adenosylmethionine, a methyl group donor used in many biological methylation reactions, including the methylation of a number of sites within DNA and RNA. Methylcobalaamin is a cofactor for L-methylmalonyl-CoA mutase. 5-Deoxyadenosylcobalamin is required by the enzyme that catalyzes the conversion of L-methylmalonyl-CoA to succinyl-CoA. This biochemical reaction plays an important role in the production of energy from fats and proteins. Succinyl CoA is also required for the synthesis of hemoglobin. Supplements as disclosed herein may include from about 0.025 to about 4.0 wt. % Vitamin B12.

Magnesium, zinc and selenium are all essential nutrients having well known functions. The supplements disclosed herein may include from about 1.0 to about 7.0 wt. % magnesium (as magnesium oxide), from about 0.025 to about 6 wt. % zinc (as zinc citrate) and from about 0.001 to about 0.02 wt. % selenium (as selenium amino acid chelate). Magnesium is an essential co-factor in many enzyme reactions in human energy and protein metabolism, its involvement as an intracellular catalyst in vital processes extends from glycolysis to the tricarboxylic acid cycle and to DNA synthesis. Magnesium is required for protein synthesis and the absorption and metabolism of calcium, sodium, phosphorus and potassium. Magnesium is required by the adenosine triphosphate (ATP) synthesizing protein in mitochondria. Magnesium also helps regulate blood sugar levels, promotes normal blood pressure.

Zinc is vital to immune resistance, wound healing, digestion, reproduction, physical growth, diabetes control, taste and smell. Zinc is necessary for the formation of certain enzymes and for enzymatic functions, carbohydrate metabolism and protein synthesis. Zinc is essential for protein synthesis and the production of cells in the body's immune system.

Selenium is an essential micronutrient with high antioxidant, antiatherogenic, antimutagenic, anticarcinogenic, and antitumour properties. Selenium is a component of many proteins, enzymes (primarily, glutathione peroxidase), and other peroxidases. Selenium is involved in the synthesis of thyroid hormone and functions as an active immunomodulator. Selenium is a potent antioxidant and protects DNA, chromosomes, biomembranes, vessel endothelium and low density lipoproteins.

In one embodiment, the supplements disclosed herein may include from about 0.01 to about 10 wt. % manganese (as manganese amino acid chelate). Manganese is necessary for bone growth, reproduction, skin, ligament formation, blood clotting, wound healing, peak brain function and the proper metabolism of cholesterol, sugars and insulin. Manganese is an enzyme activator and is reported to help in the utilization of vitamin B1. Manganese is required to produce superoxide dismutase, an enzyme used to resolve highly damaging superoxide free-radicals. Manganese is also required for proper bone and cartilage formation and some reports have shown that women with osteoporosis tend to have low blood manganese levels.

Ginger possesses antiemetic, anti-inflammatory, analgesic, and cardiotonic properties. Ginger is a cholagogic agent that promotes the flow of bile into the intestine, especially through contraction of the gallbladder. Gingerols produce concentration-dependent inotropic effects through activation of sarcoplasmic reticulum calcium adenosine triphosphatase (SR Ca2+ATPase). Ginger inhibits thromboxane synthetase and is a prostacyclin antagonist. Prostaglandins induce vasodilation and increase tissue permeability, which, in turn, promote the influx of fluids and leukocytes resulting in the classic symptoms of inflammation, e.g., swelling, redness, warmth, and pain. It is believed that at least one of the mechanisms by which ginger produces anti-inflammatory effects is through the inhibition of prostaglandin and leukotriene biosynthesis. The supplements disclosed herein may contain from about 10 to about 50 wt. % ginger root.

Acetyl-L-Carnitine, (beta-acetoxy-gamma-N, N, N-trimethylaminobutyrate), is an inducer of cytoprotective protein/enzymes (with native antioxidant effects) including heme-oxygenase-1, Hsp 70 and Super Oxide Dismutase-2 (SOD). The acetyl component of acetyl-L-carnitine provides for the formation of the neurotransmitter acetylcholine. It is believed that Acetyl-L-Carnitine inhibits apoptosis of cerebral nerve cells. It is hypothesized that the oxidative metabolism of the acetyl component of acetyl-1-carnitine reduces postischemic brain lactate levels and elevation of NIP. An antioxidant mechanism is supported by reduction of oxidative stress markers, for example, protein oxidation, in both brain tissue and cerebrospinal fluid. The mechanism of inhibiting excitotoxicity may be extremely important in neurodegenerative disorders. Animal experiments indicate that the presence of acetyl-1-carnitine significantly inhibits both acute and delayed cell death following exposure to NMDA, an excitotoxic glutamate antagonist. Several other mechanisms of action are possible, including a neurotrophic effect of acetyl-1-carnitine and inhibition of mitochondrial permeability transition. The supplements disclosed herein may contain from about 5 to about 40 wt. % acetyl-1-carnitine.

Resveratrol, (trans-3,5,4'-trihydroxystilbene), is a phytoalexin derived from grapes and other food products with antioxidant and potential chemopreventive activities. Resveratrol scavenges reactive oxygen species (ROS), decreases b-amyloid activity and promotes the breakdown of b-amyloid peptides associated with brain plaque. Resveratrol has been reported to increase SIRT1 expression (anti-aging gene) and increase cellular life in animal studies. Resveratrol interacts with nitric oxide synthase (NOS) to produce nitric oxide which scavenges OH$^-$ ions and superoxides. Resveratrol binds to aryl hydrocarbon receptors as a competitive antagonist causing preventing nuclear translocation. Resveratrol also induces phase II drug-metabolizing enzymes (anti-initiation activity), mediates anti-inflammatory effects, inhibits cyclooxygenase and hydroperoxidase functions (anti-promotion activity), and induces promyelocytic leukemia cell differentiation (anti-progression activity); thereby exhibiting activities in three major steps of carcinogenesis. The supplements disclosed herein may contain from about 1.0 to about 60 wt. % resveratrol.

In one embodiment, the supplements disclosed herein contain from about 1.0 to about 40.0 wt. % alpha lipoic acid (ALA). Alpha lipoic acid is a potent antioxidant capable of passing the blood-brain barrier. ALA is reported to improve nerve conduction attributes, endoneurial blood flow and nerve $Na^+$ $K^+$ ATPase activity in experimental diabetes testing in humans. ALA is an inhibitor of matrix metalloproteinase-9 (MMP-9) which has been linked to the degradation of elastin in arterial walls.

In one variation, the supplements may include from about 1.0 to about 40.0 wt. % coenzyme Q10. Coenzyme Q10, also referred to as ubidecarenone, is an antioxidant that plays a critical role in cellular mitochondrial generation of energy. Coenzyme Q10 acts directly as an electron carrier in oxidative phosphorylation reactions, through metabolic pathways, particularly aerobic pathways, to produce ATP and hence energy. The structure of coenzyme Q10 consists of a quinone ring attached to an isoprene side chain. Since the body must have energy available to perform even the simplest operation, coenzyme Q10 is considered essential for the body's cells, tissues, and organs. Coenzyme Q10 also has antioxidant and membrane stabilizing properties that serve to prevent the cellular damage that results from normal metabolic processes. It also stimulates the immune system, increases circulation and strengthens the cardiovascular system. Coenzyme Q10 together with other ingredients such as EGCG, resveratrol and metals (selenium, zinc and magnesium) provides synergistic neuroprotection by downregulating NF-Kappa B production.

L-Cysteine is a sulphur-bearing amino acid with antioxidant properties. L-Cysteine is synthesised internally, but requires vitamin B6 for the synthesis to take place. L-Cysteine helps to break down harmful toxins, thereby protecting and preserving cells. As an antioxidant, 1-cysteine is most effective in combination with selenium and Vitamin E. Along with selenium, 1-cysteine it is an important cofactor in the formation of glutathione peroxidase, a potent antioxidant. Without proper levels of cysteine, the body is not able to produce the amino acid glutathione, another powerful antioxidant. L-cysteine is also important for keratin synthesis, a protein found in the hair, skin and nails. It also plays a role in energy metabolism and fatty acid synthesis. The supplements disclosed herein may contain from about 2.5 to about 40 wt. % L-cysteine.

Catechins are flavanoids, polyphenolic antioxidant compounds. Catechins found in green tea are known to have a number of antioxidant activities, including scavenging of reactive oxygen species as superoxide, hydroxyl and peroxyl radicals, inhibition of lipid peroxidation, and inhibition of the oxidation of low-density lipoproteins. One catechin, epigallocatechin gallate, (EGCG) may have the greatest antioxidant activity of the green tea catechins and, in some studies, has been found to be a more potent antioxidant than ascorbate and reduced glutathione. EGCG may also have anticarcinogenic activity. EGCG has been found to induce apoptosis in some tumor cell lines and to inhibit angiogenesis. EGCG and ECG (epigallocatechin) have been demonstrated to inhibit tyrosine phosphorylation of the receptor tyrosine kinase PDGF-Rbeta (platelet-derived growth factor receptor-beta) and its downstream signaling pathway and, consequently, to inhibit transformation of human cells. The supplements disclosed herein may include from about 1 to about 40 wt. % green tea extract including catechins, in particular EGCG. In one variation, the green tea extract includes 90% catechins with 50% of the catechins being EGCG.

Citrus bioflavonoids include hesperidin, quercetin, rutin (a glycoside of quercetin), and tangeritin. These compounds exhibit antioxidant activity and the ability to increase intracellular levels of vitamin C. Hesperidin exerts beneficial effects on capillary permeability and blood flow. Hesperidin has anti-inflammatory effects and in vitro studies have demonstrated that it can cross the blood-brain barrier. The supplements disclosed herein may include from about 5 to about 40 wt. % citrus bioflavonoid, 20% of which are hesperidin.

In one embodiment, nutritional supplements are formulated in accordance with Table 1 below:

TABLE 1

| Ingredient | Weight % |
| --- | --- |
| Resveratrol | 1%-60% |
| Green Tea Extract (90% Catechins, 50% EGCG) | 1%-40% |
| Acetlyl-L-Carnitine | 5%-40% |
| Alpha Lipoic Acid | 1%-40% |
| Coenzyme Q10 | 1%-40% |
| Citrus Bioflavonoid (40% Flavonoids, 20% Hesperidin) | 5%-40% |
| Vitamin B6 (as pyridoxiyl 5 phosphate) | 0.1%-10% |

In one formulation, the above ingredients, alone or with other ingredients, may be combined, for example by encapsulation, as follows:

TABLE 2

| Ingredient | Weight |
| --- | --- |
| Resveratrol | 10 mg. |
| Green Tea Extract (90% Catechins, 50% EGCG) | 25 mg |
| Acetlyl-L-Carnitine | 50 mg |
| Alpha Lipoic Acid | 50 mg |
| Coenzyme Q10 | 25 mg |
| Citrus Bioflavonoid (40% Flavonoids, 20% Hesperidin) | 100 mg |
| Vitamin B6 | 5 mg. |
| Total | 265 mg |

A recommended daily dosage of the supplement of Table 2 is from one to three capsules (about 530 to 795 mg/day). Accordingly, desired daily dosages of supplements containing the ingredients listed in Table 2 include from about 10 to about 30 mg of resveratrol, from about 12.5 to about 37.5 mg. EGCG (from green tea extract), from about 50 to about 150 mg of acetyl-1-carnitine, from about 50 to about 150 mg of alpha lipoic acid, from about 25 to about 75 mg. of coenzyme Q10, from about 20 to about 60 mg of hesperidin (from citrus bioflavonoids) and from about 5 to about 15 mg of vitamin B6.

In other formulations, nutritional supplements may be formulated with a number of additional supportive and/or synergistic enhancers including thiamin, folic acid, vitamin B12, magnesium, zinc, selenium, manganese, ginger root P.E 4:1, and 1-cysteine. Formulations including such supportive and/or synergistic enhancers may include the ingredients and in the amounts set forth in Table 3, below:

TABLE 3

| Ingredient | Weight % |
| --- | --- |
| Thiamin (as thiamin hydrochloride) | 0.25%-6.0 |
| Vitamin B6 (as pyridoxiyl 5 phosphate) | 0.1%-10% |

TABLE 3-continued

| Ingredient | Weight % |
|---|---|
| Folic Acid | 01%-10% |
| Vitamin B12 (as hydroxycobalamin) | 0.025%-4.0% |
| Magnesium (as magnesium oxide) | 1%-7% |
| Zinc (as zinc citrate) | 0.25%-6.0% |
| Selenium (as selenium amino acid chelate) | 0.001%-0.02% |
| Manganese (as manganese amino acid chelate) | 0.01%-10% |
| Ginger Root P.E 4:1 | 5%-50% |
| *Citrus* Bioflavonoid (40% Flavonoids, 20% Hesperidin) | 5%-40% |
| L-Cysteine | 2.5%-40% |
| N-Acetlyl-L-Carnitine | 5%-40% |
| Alpha Lipoic Acid | 1%-40% |
| Coenzyme Q10 | 1%-40% |
| Green Tea Extract (90% Catechins, 50% EGCG) | 1%-40% |
| Resveratrol | 1%-60% |

In a preferred form, a nutritional supplement is formulated in accordance the amounts listed in Table 4:

TABLE 4

| Ingredient | Amount | Weight % |
|---|---|---|
| Thiamin (as thiamin hydrochloride) | 5 mg | 0.66% |
| Vitamin B6 (as pyridoxiyl-5-phosphate) | 5 mg | 0.66% |
| Folic Acid | 800 mcg | 0.01% |
| Vitamin B12 (as hydroxycobalamin) | 1 mg | 0.13% |
| Magnesium (as magnesium oxide) | 25 mg | 3.28% |
| Zinc (as zinc citrate) | 10 mg | 1.31% |
| Selenium (as selenium amino acid chelate) | 20 mcg | 0.003% |
| Manganese (as manganese amino acid chelate) | 250 mcg | 0.03% |
| Ginger Root P.E 4:1 | 250 mg | 32.81% |
| *Citrus* Bioflavonoid (40% flavonoids, 20% hesperidin) | 100 mg | 13.12% |
| L-Cysteine | 100 mg | 13.12% |
| N-Acetlyl-L-Carnitine | 150 mg | 19.68% |
| Alpha Lipoic Acid | 50 mg | 6.56% |
| Coenzyme Q10 | 25 mg | 3.28% |
| Green Tea Extract (90% Catechins, 50% EGCG) | 25 mg | 3.28% |
| Resveratrol | 15 mg | 1.97% |
| Total | 762.1 mg | 100.00% |

The preferred daily dosage of the supplement of Table 4 is in the range of from one to three capsules (about 760 to about 2290 mg/day) with the ingredients in the amounts listed in Table 4 above. Accordingly, the daily dosages of the ingredients may comprise 5 to 15 mg thiamin, 5 to 15 mg pyridoxiyl-5-phosphate, 800 to 2400 mcg folic acid, 1 to 3 mg hydroxycobalamin, 25 to 75 mg magnesium, 10 to 30 mg zinc, 20 to 60 mcg selenium, 250 to 750 mcg manganese, 250 to 750 mg ginger root RE 4:1, 100 to 300 mg citrus bioflavonoids, 100 to 300 mg 1-cysteine, 150 to 450 mg n-acetlyl-1-carnitine, 50 to 150 mg alpha lipoic acid, 25 to 75 mg coenzyme Q10, 25 to 75 mg green tea extract and 15 to 45 mg resveratrol.

The above supplements may be prepared in an ingestible solid form such as capsules tablets, pills or granules. In the solid form, the ingredients may be admixed with fillers, binders and humectants. Additional ingredients may include preservatives, wetting agents, flow agents and emulsifiers and other components such as gelatin, glycerin, water, stearic acid, silicon dioxide, and magnesium stearate. The supplements may also be prepared as a liquid solution.

The supplements disclosed above protect cochlear and labyrinthine cellular integrity and physiologic function through a variety of mechanisms that operate on a tissue, cellular, and sub cellular level. Cell membrane stability and integrity is promoted along with cytoprotection from hazardous metabolites including but not restricted to oxygen free radicals. The supplements promote immunologic modification to prevent immune mediated damage to inner ear cells. Efficient and appropriate cell messenger system operation are promoted with systems such as NO (nitric oxide) and ceramide synthases. The supplements also help regulate apoptosis (planned cell death at senescence). Regulation of apoptosis is important in cochlear cell health maintenance by preventing cell/neuron death as a result of what should be sublethal insult. Alternatively, apoptosis is upregulated in conditions of carcinogenesis and true cell senescence.

Protection and facilitation of mitochondrial function, health, and stability are provided by the supplements disclosed herein. Modulation of platelet function which may include reduction of thrombosis of macro and microcirculation is promoted as is improved blood flow via improved vascular smooth muscle function. Protection from cellular ischemia is provided by promoting production of protective molecules such as adenosine from cells.

The supplements disclosed herein promote proper function of supporting cells of the inner ears by facilitating proper function of cell membrane pumps and other elements maintaining biologic electro-potential of cell fluid spaces. The supplements decrease proinflammatory leukotrienes and prostaglandins, matrix metalloproteinase 9 (MMP-9), an actor in neuron injury and death, and microvascular injury. MMP-9 is a gelatinase produced by inflammatory and resident brain cells in a variety of central nervous system (CNS) inflammatory conditions, in animals and humans. MMP-9 promotes meningeal inflammation, breakdown of the blood brain barrier, and vasculitis.

Neural plaque and amyloid formation is inhibited and existing plaque regression promoted though the use of supplements formulated as disclosed herein. The supplements upregulate transcription and production of phase II proteins (critical in native cellular defense mechanisms). Injury secondary to ischemia is minimized or prevented through metabolic regulation, decreased tissue activity, and protection during reperfusion.

A number of ingredients act synergistically to achieve the foregoing. For example, hepatic and duodenal sulphation are believed to limit the bioavailability of resveratrol. The citric flavanoids contained in the compounds enhance bioavailability of resveratrol through inhibition of sulphation in the liver.

Homocysteine permanently degrades cysteine (disulfide bridges) and lysine amino acid residues in proteins, gradually affecting cell function and structure. It has been reported that the combination of folate with vitamins B6 or B12 modulates occlusive vascular disease. The supplements disclosed herein combine folic acid with vitamin B12 to achieve this effect.

Resveratrol and catechin are reported to have different activities on the signal transduction pathway involving protein phosphorylation. The different activities are believed to result in a synergistic effect against beta-AP (1-41) toxicity, e.g., plaque in Alzheimer's and other neurodegenerative diseases. The different activity of resveratrol and catechin on signal transduction pathways, the differences in metal chelation, effect on partition coefficient between water and lipids, hydrogen donation redox potential and enzyme inhibition may be at least in part based on synergistic protection against beta-AP (1-41) toxicity. The supplements disclosed herein provide this effect with a combination of resveratrol and green tea extract.

Patients having meniere's disease treated with nutritional supplements as disclosed herein were observed to have decreased dizziness, improved hearing and, in some cases, decreased tinnitus. Patients exposed to loud noises were observed to have a more rapid return to baseline hearing when treated with supplements as disclosed herein. Some patients were observed to have stabilized or improved tone testing when treated with the supplements.

It will be appreciated by those skilled in the art having the benefit of this disclosure that the supplements disclosed herein stabilize and protect the cochlear system, inhibiting sensorineural hearing loss. It should be understood that detailed description herein is to be regarded in an illustrative rather than a restrictive manner, and is not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. An ingestible solid nutritional supplement comprising:

| | |
|---|---|
| 0.25%-6.0% | Thiamin |
| 0.1%-10% | Vitamin B6 |
| 0.01%-10% | Folic Acid |
| 0.025%-4.0% | Vitamin B12 |
| 1%-7% | Magnesium |
| 0.25%-6.0% | Zinc |
| 0.001%-0.02% | Selenium |
| 0.01%-10% | Manganese |
| 5%-50% | Ginger Root P.E. |
| 5%-40% | Citrus Bioflavonoid |
| 2.5%-40% | L-Cysteine |
| 5%-40% | N-Acetyl-L-Carnitine |
| 1%-40% | Alpha Lipoic Acid |
| 1%-40% | Coenzyme Q10 |
| 1%-40% | Green Tea Extract |
| 1%-60% | Resveratrol; | wherein the solid nutritional supplement is in the form of capsules, tablets, pills or granules with ingredients selected from the group consisting of fillers, binders, humectants, preservatives, wetting agents, flow agents and emulsifiers; wherein the weight ratio of alpha lipoic acid to citrus bioflavonoid to N-acetyl-L-carnitine to ginger root P.E is 1:2:3:5; and the solid nutritional supplement treats sensorineural hearing loss.

2. The nutritional supplement of claim 1 wherein the citrus bioflavonoids comprise about 20 wt. % hesperidin.

3. The nutritional supplement of claim 1 wherein the EGCG is provided in the form of green tea extract comprising 90 wt. % catechins and wherein the catechins comprise about 50 wt. % EGCG.

4. The nutritional supplement of claim 1 further comprising from about 0.1-10 wt. % folic acid.

5. The nutritional supplement of claim 1 wherein the magnesium is present as magnesium oxide and the zinc is present as zinc citrate.

6. The nutritional supplement of claim 1 wherein the selenium is present as selenium amino acid chelate and the manganese is present as manganese amino acid chelate.

* * * * *